(12) United States Patent
Liaw et al.

(10) Patent No.: US 11,224,393 B2
(45) Date of Patent: Jan. 18, 2022

(54) FLUOROSCOPY SYSTEM

(71) Applicants: Chen-Kun Liaw, Taipei (TW); Tai-Yin Wu, Taipei (TW)

(72) Inventors: Chen-Kun Liaw, Taipei (TW); Tai-Yin Wu, Taipei (TW); Yu-Ciao Liao, Taipei (TW); Yu-Yan Liao, Taipei (TW); Hsiang-Hung Liaw, Taipei (TW); Yu-Peng Liao, Taipei (TW)

(73) Assignees: Chen-Kun Liaw, Taipei (TW); Tai-Yin Wu, Taipei (TW)

( * ) Notice: Subject to any disclaimer, the term of this patent is extended or adjusted under 35 U.S.C. 154(b) by 0 days.

(21) Appl. No.: 17/000,388

(22) Filed: Aug. 24, 2020

(65) Prior Publication Data
US 2021/0052239 A1 Feb. 25, 2021

Related U.S. Application Data

(60) Provisional application No. 62/891,278, filed on Aug. 24, 2019.

(51) Int. Cl.
| | |
|---|---|
| *A61B 34/10* | (2016.01) |
| *A61B 5/00* | (2006.01) |
| *A61B 6/00* | (2006.01) |
| *A61B 6/08* | (2006.01) |

(52) U.S. Cl.
CPC ............... *A61B 6/485* (2013.01); *A61B 6/08* (2013.01); *A61B 6/4441* (2013.01); *A61B 6/461* (2013.01)

(58) Field of Classification Search
CPC .................. A61B 32/10; A61B 5/0059; A61B 2034/1074; A61B 34/20; A61B 6/4078; A61B 6/42; A61B 6/5205; A61B 6/12; A61B 2034/2055; A61B 6/461; A61B 6/54; A61B 6/487; A61B 6/4085; A61B 6/032; A61B 6/4441; A61N 2005/1074; A61N 5/1068; A61N 5/1067; A61N 2055/1059
See application file for complete search history.

(56) References Cited

U.S. PATENT DOCUMENTS

2016/0166333 A1* 6/2016 Wang ..................... A61B 90/11
600/476

* cited by examiner

*Primary Examiner* — Don K Wong

(57) ABSTRACT

A fluoroscopy system includes a fluoroscopy device, an indicating assembly and a center control device. The fluoroscopy device includes a contoured support arm, an X-ray emitting unit, an X-ray sensor and a display unit. The contoured support arm has a first end part and a second end part opposite to the first end part. The X-ray emitting unit is located on the first end part and is configured to emit an X-ray. The X-ray sensor is located on the second end part to sense the X-ray. The display unit is electrically connected to the X-ray sensor. The indicating assembly is located near the contoured support arm and includes a plurality of light emitting units. Each of the plurality of light emitting units is rotatable and configured to emit a light plane. The center control device is electrically connected to the fluoroscopy device and the indicating assembly.

8 Claims, 5 Drawing Sheets

FLUOROSCOPY SYSTEM

FIELD OF THE INVENTION

The present invention relates to a fluoroscopy system, and more particularly to a fluoroscopy system for surgery.

BACKGROUND OF THE INVENTION

A fluoroscopy device is a type of medical imaging that shows continuous X-ray images on a monitor. During a fluoroscopy procedure, an X-ray beam can be passed through the patient. An X-ray image is transmitted to the monitor. For example, during an orthopaedic operation, the surgeons can see the reduction and the implants position immediately by the fluoroscopy device.

A fluoroscopy operator needs sufficient experience and sense of space to shoot qualified X-ray images for the surgeons, otherwise more X-ray images may be shot. Thereby exposing the surgeons, patient and the fluoroscopy operator to additional radiation.

Conventionally, a laser aiming device for emitting a laser beam from an X-ray tube to an X-ray sensor of a fluoroscopy device is used. However, the laser beam of the laser aiming device is not functional for a demand of slightly moving the C-arm to aim a special target shown on a monitor.

Further, when a hardware such as a Kirschner wire, is going to be implanted into a bone in an orthopaedic operation, the surgeons may need additional three to four shots X-ray images to place the hardware to a correct position.

Computer navigation is another solution for a fluoroscopy procedure. However, computer navigation is very expensive and needs addition bulky equipment. Accordingly, computer navigation is not practical for daily practice.

SUMMARY OF THE INVENTION

The present invention provides a fluoroscopy system including a fluoroscopy device, an indicating assembly and a center control device. The fluoroscopy device includes a contoured support arm, an X-ray emitting unit, an X-ray sensor and a display unit. The contoured support arm has a first end part and a second end part opposite to the first end part. The X-ray emitting unit is located on the first end part and is configured to emit an X-ray. The X-ray sensor is located on the second end part to sense the X-ray. The display unit is electrically connected to the X-ray sensor. The indicating assembly is located near the contoured support arm and includes a plurality of light emitting units. Each of the plurality of light emitting units is rotatable and configured to emit a light plane. The center control device is electrically connected to the fluoroscopy device and the indicating assembly. The center control device is configured to control a rotation angle of each of the plurality of light emitting units, and the light planes respectively emitted by at least two of the plurality of light emitting units intersect to form an indicating light stream overlapping a line from the X-ray emitting unit to a predetermined point on the X-ray sensor. The indicating light stream is displayed on the display unit as an indicating point.

In an embodiment of the present invention, the number of the plurality of light emitting units is five, two of the light emitting units are located near the X-ray emitting unit, and three of the light emitting units are located near the X-ray sensor.

In an embodiment of the present invention, the three light emitting units located near the X-ray sensor are used to form the indicating light stream, thereby forming the indicating point on the display unit.

In an embodiment of the present invention, the two light emitting units located near the X-ray emitting unit are used to form the indicating light stream, thereby forming the indicating point on the display unit.

In an embodiment of the present invention, each of the plurality of light emitting units is a laser projector.

In an embodiment of the present invention, the central control device is configured to detect if the X-ray image formed on the X-ray sensor is rotated.

In an embodiment of the present invention, when a point of the display unit is pointed, the center control device is configured to calculate a position corresponding to the point on the X-ray sensor, calculate rotation angles of the light emitting units and send rotation signals to the light emitting units.

In an embodiment of the present invention, the center control device is configured to detect and correct a torsion formed on the display unit.

Comparing to a conventional fluoroscopy device, the fluoroscopy system of the embodiments of the invention additionally comprises the indicating assembly and the center control device. The indicating assembly and the center control device are not expensive and can be easily equipped. In addition, the indicating assembly can form an indicating point on the display unit, and a fluoroscopy operator can see a current position aimed by the X-ray emitting unit on the display unit, thereby the following operation can be guided by the indicating point, or the contoured support arm can be adjusted in accordance with the indicating point. In addition, when a point corresponding to a new target is pointed on the display unit, the central control unit can automatically calculate the corresponding rotation angles of the light emitting units, even the new target is simply moved a small distance from an original target. In addition, the surgeons may only need one or two times to accurately place a hardware into a bone by the guiding of the indicating point shown on the display unit in an orthopaedic operation.

BRIEF DESCRIPTION OF THE DRAWINGS

The present invention will become more readily apparent to those ordinarily skilled in the art after reviewing the following detailed description and accompanying drawings, in which.

DETAILED DESCRIPTION OF PREFERRED EMBODIMENTS

The present invention will now be described more specifically with reference to the following embodiments. It is to be noted that the following descriptions of preferred embodiments of this invention are presented herein for purpose of illustration and description only. It is not intended to be exhaustive or to be limited to the precise form disclosed.

Figure 1A:
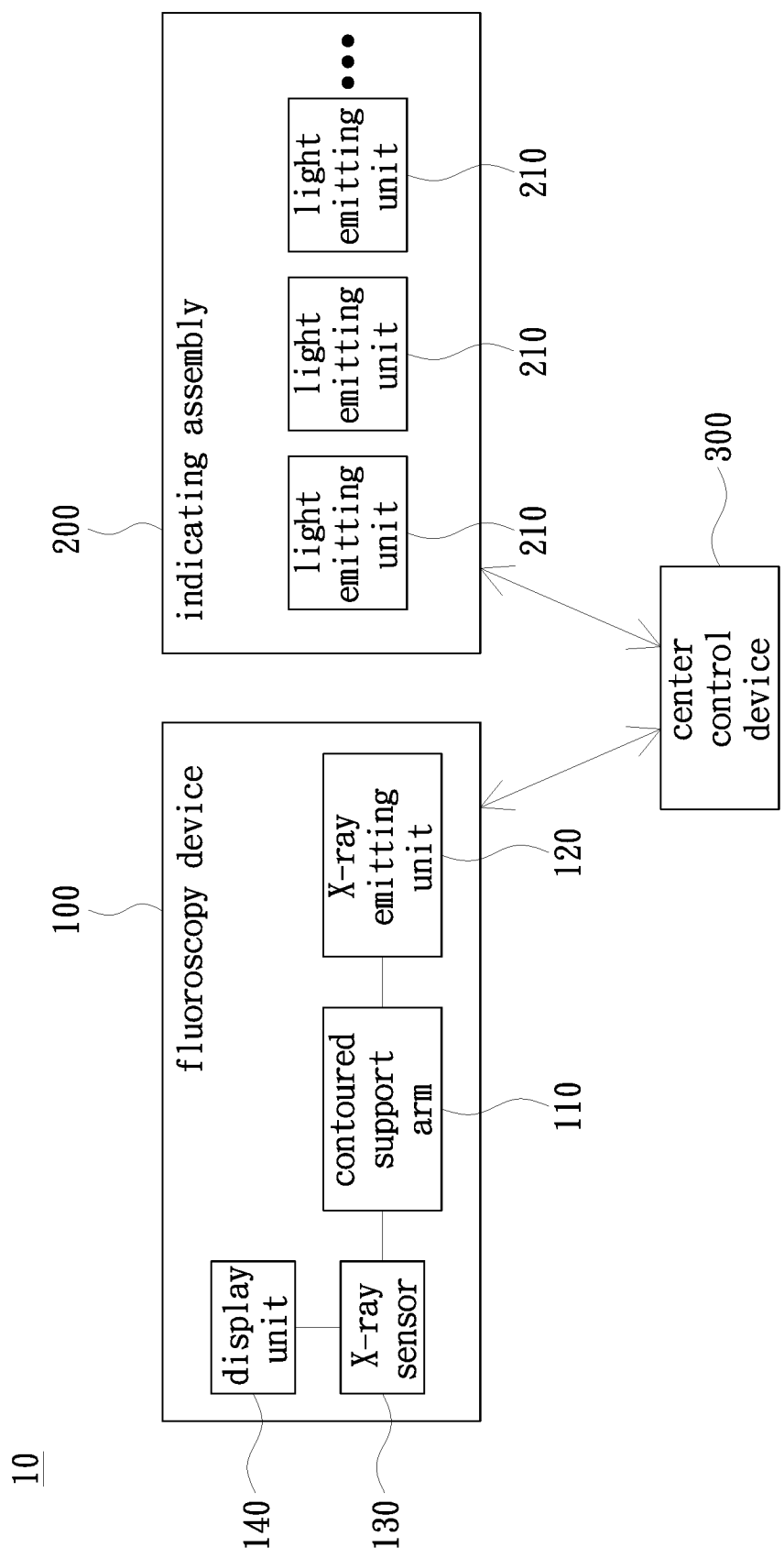
FIG. 1A is a schematic block diagram of a fluoroscopy system of an embodiment of the present invention.
Figure 1B:
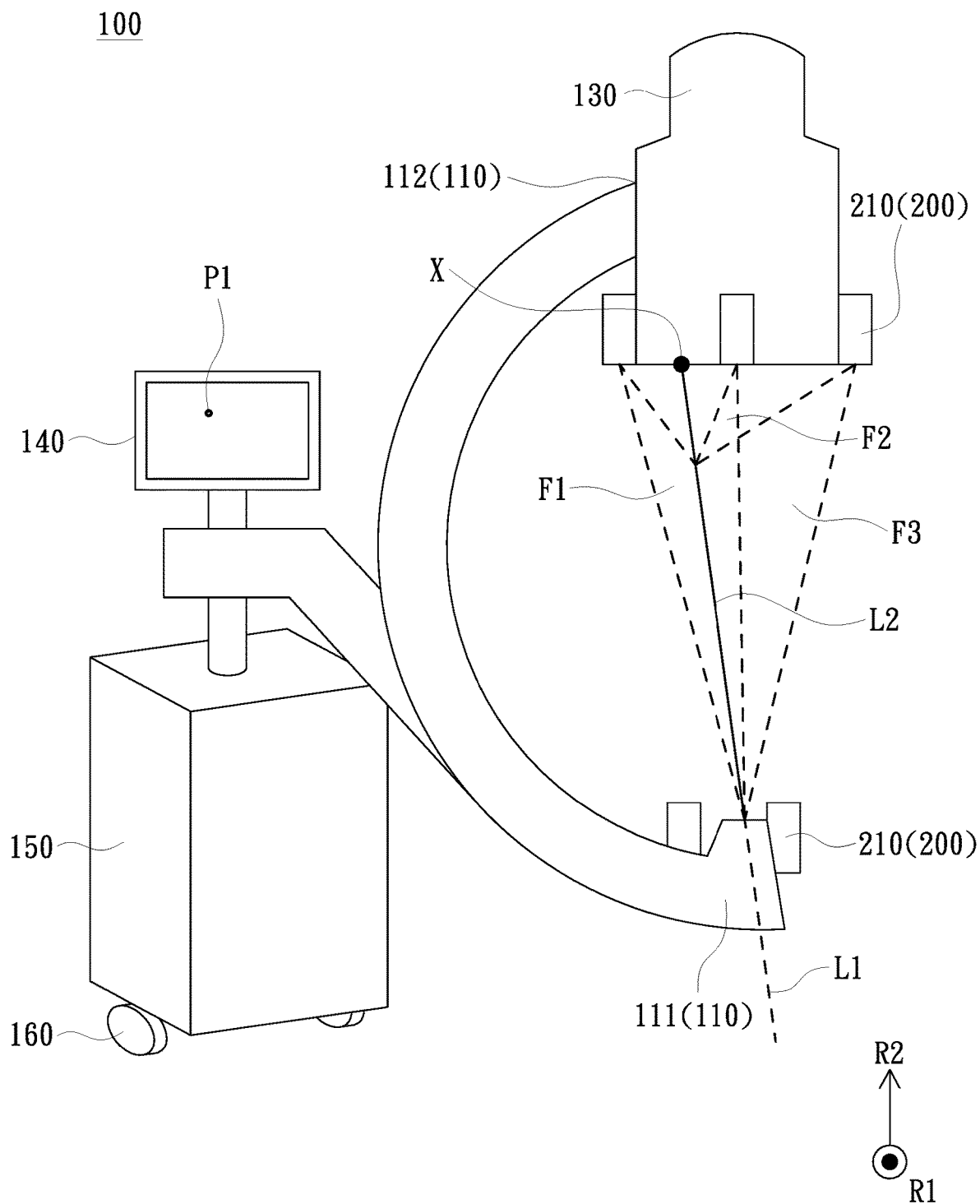
FIG. 1B is a schematic diagram of the fluoroscopy and the indicating device of FIG. 1A.
Figure 1C:
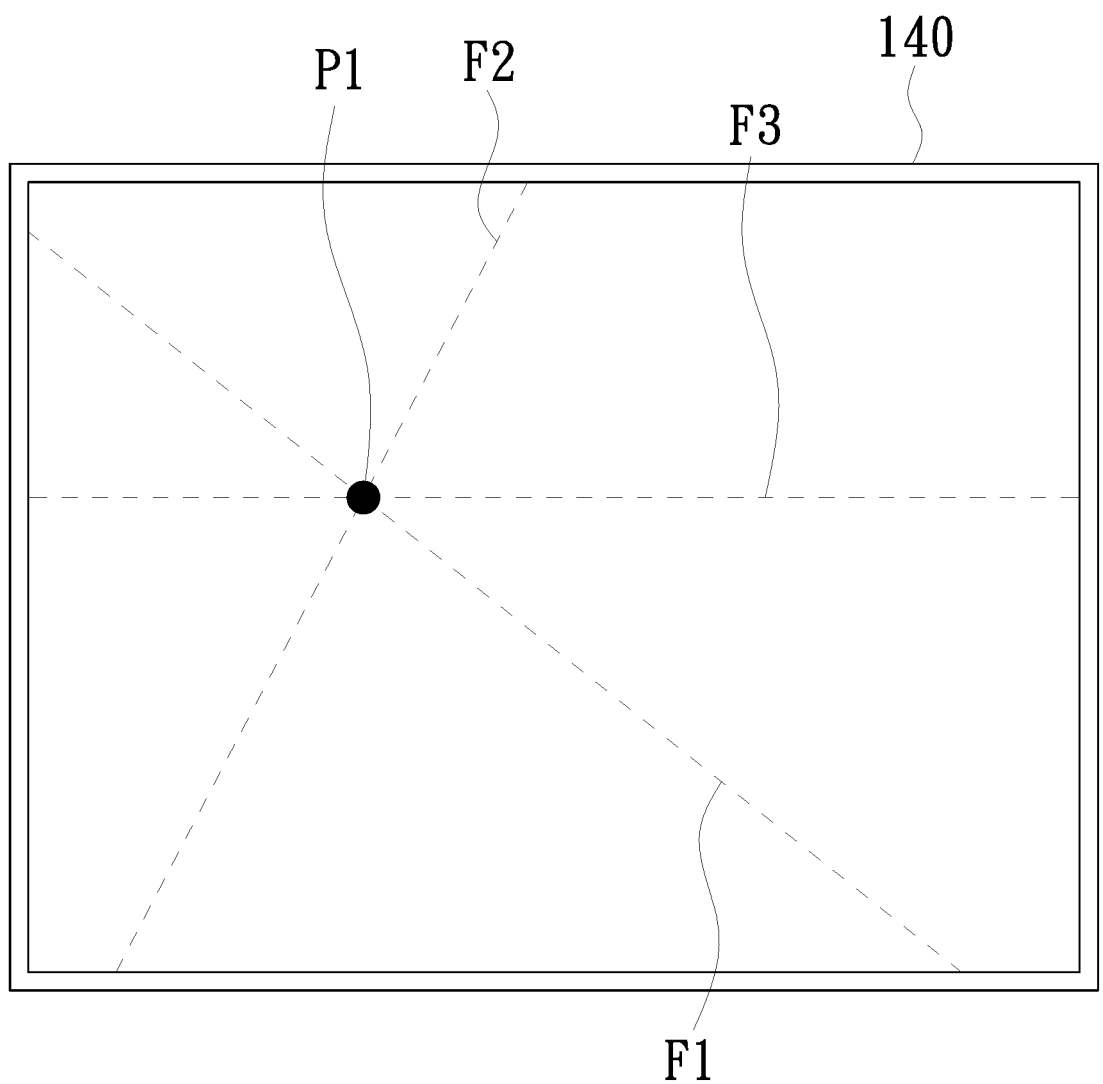
FIG. 1C is an enlarged schematic diagram of the display unit of FIG. 1B.
Figure 1D:
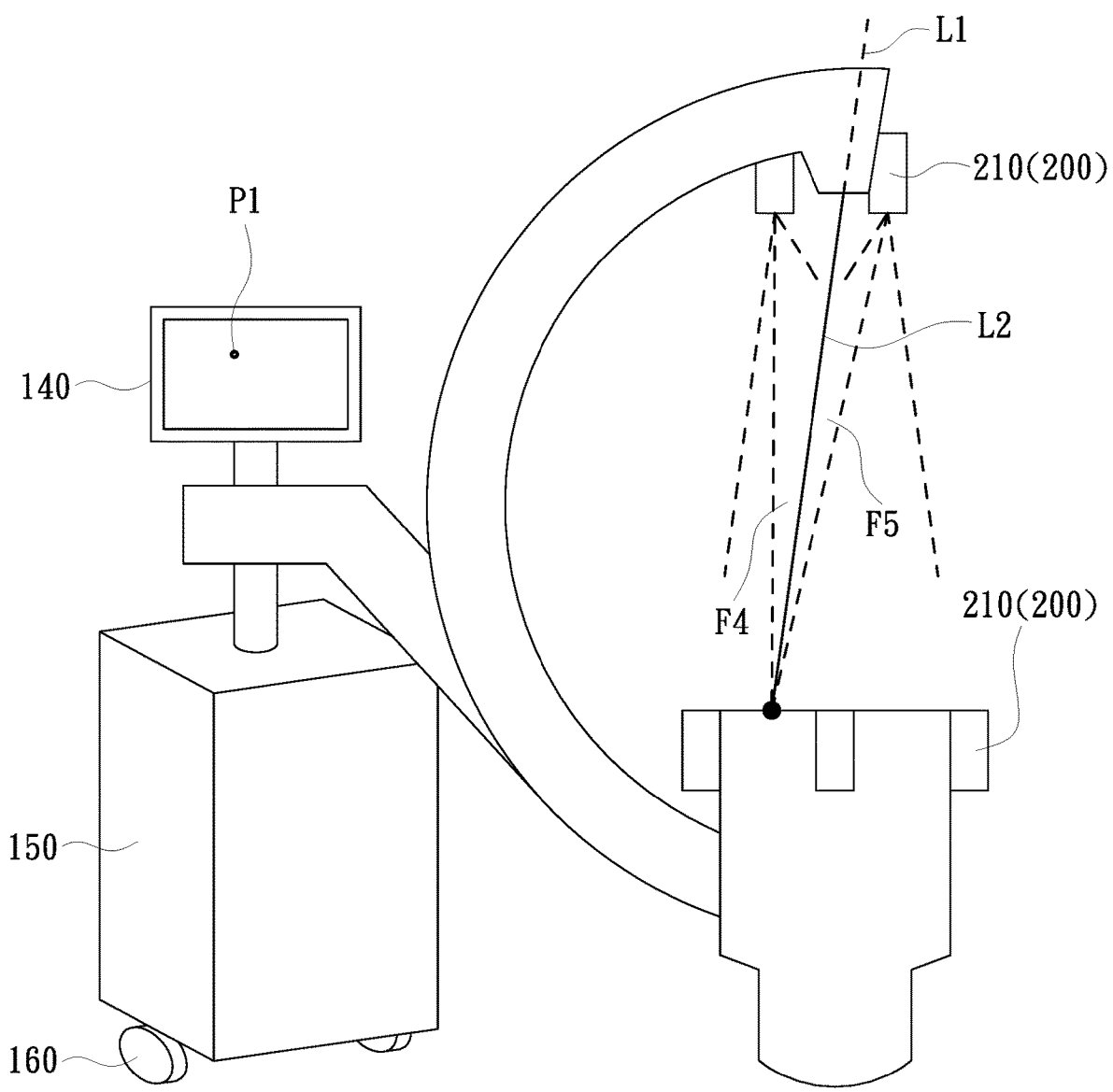
FIG. 1D is another schematic diagram of the fluoroscopy and the indicating device of FIG. 1A.

FIG. 1A is a schematic block diagram of a fluoroscopy system of an embodiment of the present invention. FIG. 1B is a schematic diagram of the fluoroscopy and the indicating device of FIG. 1A. FIG. 1C is an enlarged schematic diagram of the display unit of FIG. 1B. FIG. 1D is another schematic diagram of the fluoroscopy and the indicating device of FIG. 1A. FIG. E is an enlarged schematic diagram of the display unit of FIG. 1D. Please refer to FIGS. 1A to 1E, a fluoroscopy system 10 of the embodiment includes a fluoroscopy device 100, an indicating assembly 200 and a center control device 300.

The fluoroscopy device 100 includes a contoured support arm 110, an X-ray emitting unit 120, an X-ray sensor 130 and a display unit 140. The contoured support arm 110 has a first end part 111 and a second end part 112 opposite to the first end part 111. The X-ray emitting unit 120 is located on the first end part 111 and is configured to emit an X-ray. The X-ray sensor 130 is located on the second end part 112 to sense the X-ray to form an X-ray image. The display unit 140 is electrically connected to the X-ray sensor 130 to display the X-ray image.

In the embodiment, the contoured support arm 110 is moveable. The contoured support arm 110 may rotate about a first rotation axis R1 and a second rotation axis R2 perpendicular to the first rotation axis R1. In addition, the fluoroscopy device 100 further includes a base 150 and a plurality of wheels 160 disposed on a bottom of the base 150. The contoured support arm 110 can be laterally moved with the base 150.

The indicating assembly 20 is located near the contoured support arm 110 and includes a plurality of light emitting units 210. Each of the plurality of light emitting units 210 is rotatable and configured to emit a light plane. In the embodiment, the number of the plurality of light emitting units 210 is five, two of the light emitting units 210 are located near the X-ray emitting unit 120, and three of the light emitting units 210 are located near the X-ray sensor 130. But is not limited there to. In the embodiment, each of the plurality of light emitting units 210 is a laser projector, but is not limited thereto. In the embodiment, the light emitting units 210 are attached to the X-ray emitting unit 120 or the X-ray sensor 130. However, in another embodiment, the indicating assembly 200 may include a bracket (not shown) independent the fluoroscopy device 100 to support the light emitting units 210.

The center control device 300 is electrically connected to the fluoroscopy device 100 and the indicating assembly 200. The center control device 300 is configured to control a rotation angle of each of the plurality of light emitting units 210, and the light planes respectively emitted by at least two of the plurality of light emitting units 210 intersect to form an indicating light stream L2 overlapping a line L1 from the X-ray emitting unit 120 to a predetermined point X on the X-ray sensor 130. The indicating light stream L2 is displayed on the display unit 140 as an indicating point P1. The center control device 300 can be a computer or a server.

A patient (not shown) laying on a bed (not shown) may be located between the X-ray emitting unit 120 and the X-ray sensor 130, and the light stream L2 and may project to the patient.

As shown in FIGS. 1B and 1C, three light emitting units 210 near the X-ray sensors 130 are used to form a light plane F1, a light plane F2 and a light plane F3 to intersect the indicating light stream L2, thereby forming the indicating point P1 shown on the display unit 140.

Figure 1E:
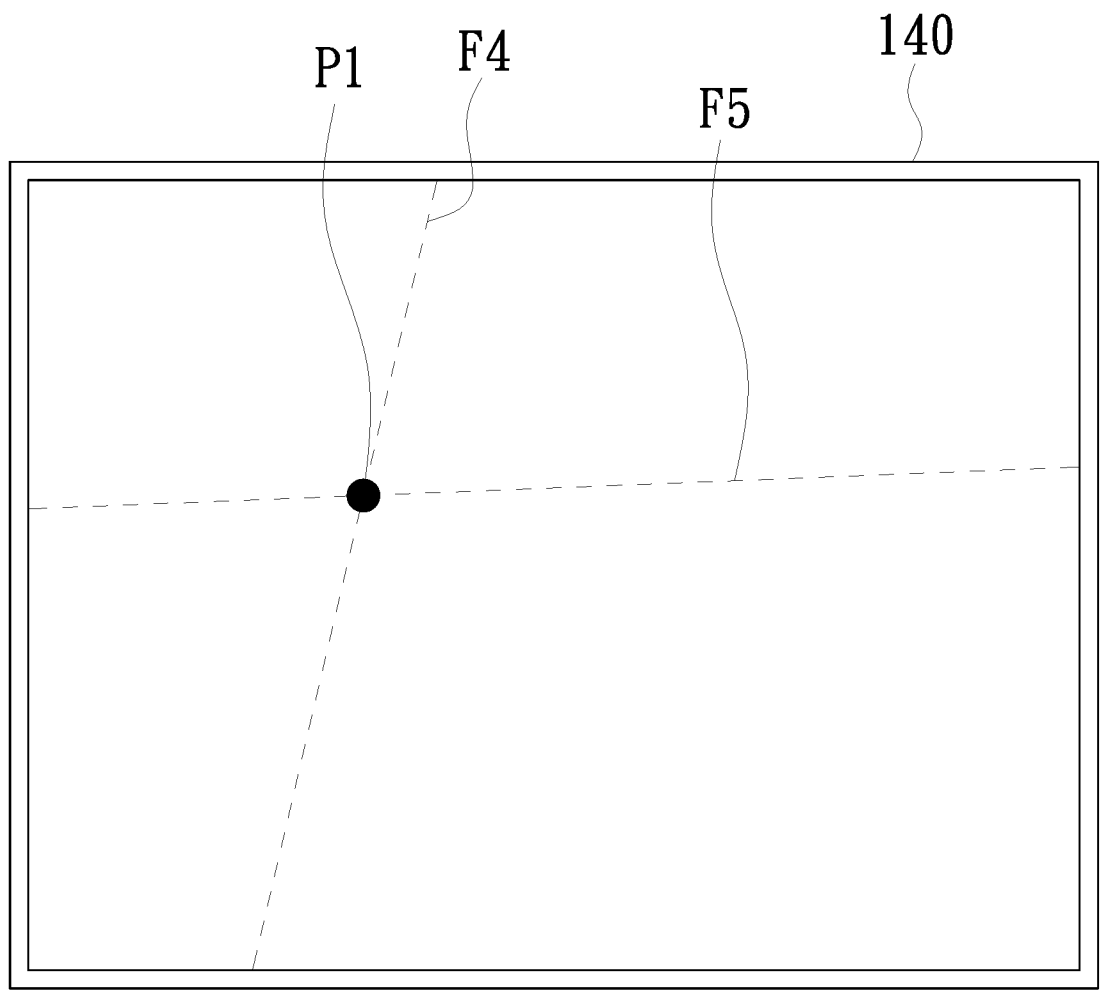
FIG. 1E is an enlarged schematic diagram of the display unit of FIG. 1D.

As shown in FIGS. 1D and 1E, two light emitting units 210 near the X-ray emitting unit 120 are used to form a light plane F4 and a light plane F5 to intersect the indicating light stream L2, thereby forming the indicating point P1 shown on the display unit 140.

In the embodiment, the X-ray image formed on the X-ray sensor 130 may be automatically rotated, and the central control device 300 is also configured to detect if an X-ray image formed on the X-ray sensor 130 is rotated.

In the embodiment, the predetermined point X can be decided by pointing a point such as P1 on the display unit 140, the center control device 300 can calculate a position of the predetermined point X on the X-ray sensor 130, calculate the corresponding rotation angles of the light emitting units 210 and send rotation signals to the light emitting units 210.

In the embodiment, the central control device 300 is also configured to detect and correct a torsion of display unit 140 to improve the quality of X-ray images. The central control device 300 may correct the torsion after reading the pointed point on the display unit and before calculating the corresponding rotation angles of the light emitting units 210.

Comparing to a conventional fluoroscopy device, the fluoroscopy system of the embodiments of the invention additionally comprises the indicating assembly and the center control device. The indicating assembly and the center control device are not expensive and can be easily equipped. In addition, the indicating assembly can form an indicating point on the display unit, and a fluoroscopy operator can see a current position aimed by the X-ray emitting unit on the display unit, thereby the following operation can be guided by the indicating point, or the contoured support arm can be adjusted in accordance with the indicating point. In addition, when a point corresponding to a new target is pointed on the display unit, the central control unit can automatically calculate the corresponding rotation angles of the light emitting units, even the new target is simply moved a small distance from an original target. In addition, the surgeons may only need one or two times to accurately place a hardware into a bone by the guiding of the indicating point shown on the display unit in an orthopaedic operation.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:
1. A fluoroscopy system, comprising:
   a fluoroscopy device, comprising a contoured support arm, an X-ray emitting unit, an X-ray sensor and a display unit, wherein the contoured support arm has a first end part and a second end part opposite to the first end part, the X-ray emitting unit is located on the first end part and is configured to emit an X-ray, the X-ray sensor is located on the second end part to sense the X-ray to form an X-ray image, the display unit is electrically connected to the X-ray sensor to display the X-ray image;
   an indicating assembly, located near the contoured support arm and comprising a plurality of light emitting units, wherein each of the plurality of light emitting units is rotatable and configured to emit a light plane; and a center control device, electrically connected to the fluoroscopy device and the indicating assembly;

wherein the center control device is configured to control a rotation angle of each of the plurality of light emitting units, and the light planes respectively emitted by at least two of the plurality of light emitting units intersect to form an indicating light stream overlapping a line from the X-ray emitting unit to a predetermined point on the X-ray sensor;

wherein the indicating light stream is displayed on the display unit as an indicating point.

2. The fluoroscopy system according to claim 1, wherein the number of the plurality of light emitting units is five, two of the light emitting units are located near the X-ray emitting unit, and three of the light emitting units are located near the X-ray sensor.

3. The fluoroscopy system according to claim 2, wherein the three light emitting units located near the X-ray sensor are used to form the indicating light stream, thereby forming the indicating point on the display unit.

4. The fluoroscopy system according to claim 2, wherein the two light emitting units located near the X-ray emitting unit are used to form the indicating light stream, thereby forming the indicating point on the display unit.

5. The fluoroscopy system according to claim 1, wherein each of the plurality of light emitting units is a laser projector.

6. The fluoroscopy system according to claim 1, wherein the central control device is configured to detect if the X-ray image formed on the X-ray sensor is rotated.

7. The fluoroscopy system according to claim 1, wherein the predetermined point is decided by pointing a point on the display unit, the center control device is configured to calculate a position of the predetermined point on the X-ray sensor, calculate corresponding rotation angles of the light emitting units and send rotation signals to the light emitting units.

8. The fluoroscopy system according to claim 7, wherein the center control device is configured to detect and correct a torsion formed on the display unit.

* * * * *